United States Patent [19]
Rankin et al.

[11] Patent Number: 4,911,151
[45] Date of Patent: Mar. 27, 1990

[54] DISPOSABLE DRESSING COVER

[76] Inventors: Paul Rankin, 1536 Conneaut Ave., Bowling Green, Ohio 43402; Peter A. Lepovsky, 21 Olde Commond Dr., Atkinson, N.H. 03911-1030

[21] Appl. No.: 283,460

[22] Filed: Dec. 12, 1988

[51] Int. Cl.⁴ .............................................. A61F 13/00
[52] U.S. Cl. ........................................ 128/82; 128/849
[58] Field of Search ............... 128/849, 82, 87 R, 821, 128/83

[56] References Cited

U.S. PATENT DOCUMENTS

| | | | |
|---|---|---|---|
| 3,324,580 | 6/1967 | Baxter | 36/8.1 |
| 3,741,203 | 6/1973 | Liman | 128/82 |
| 3,747,125 | 7/1973 | Goldman et al. | 2/240 |
| 3,906,941 | 9/1975 | Cook, Jr. | 128/82 |
| 4,043,326 | 8/1977 | Little et al. | 128/82 |
| 4,139,003 | 2/1979 | Little et al. | 128/82 |
| 4,254,765 | 3/1981 | Brown et al. | 128/82 |
| 4,562,834 | 1/1986 | Bates et al. | 128/82 |
| 4,727,864 | 3/1988 | Wiesenthal et al. | 128/82 |

Primary Examiner—Robert A. Hafer
Assistant Examiner—Lynda M. Cofsky
Attorney, Agent, or Firm—Gifford, Groh, Sprinkle, Patmore and Anderson

[57] ABSTRACT

A disposable waterproof covering for a cast or bandage on an arm or leg to be used primarily when bathing or showering to protect against wetting the cast or bandage. A generally tubular plastic sleeve is sealed to the user's arm or leg above the cast or bandage by a flexible plastic strap to effect a snug, water-tight contact of the sleeve with the arm or leg. The strap is secured by an adhesive at one end to the sleeve adjacent the open end of the sleeve and wound around 360° and secured at its other by a pressure sensitive adhesive.

3 Claims, 1 Drawing Sheet

DISPOSABLE DRESSING COVER

BACKGROUND OF THE INVENTION

Field of the Invention

This invention relates to a protective limb covering, and, more particularly, to a disposable waterproof covering to cover and seal a cast or bandage on a leg or arm to permit bathing or showering without damage to the cast or bandage or further irritation to the injury.

Description of the Prior Art

There are a wide variety of bandages or cast covers which are intended to provide a waterproof covering for bathing purposes. Some of these covers are so complex as to hardly afford a disposable product. For example, U.S. Pat. No. 3,741,203 to Liman provides a covering complete with a foam rubber sealing layer, inner bag with valve for inflation, and zipper and adhesive tape closures. Other closures of the reusable type require a good deal of dexterity or time in their application so as to be a source of irritation to the user. Thus U.S. Pat. No. 3,906,941 to Cook, Jr. with its wrap around band and rubber band lock, and U.S. Pat. No. 4,139,003 to Little, et al. with its roll-up sleeve may fall in this category.

Attempts to provide a simpler but still reusable covering have taken the form of using adhesive tape to seal entirely around both the waterproof sleeve and the user's limb. This results in the formation of leakage channels particularly at the point of tape overlap. U.S. Pat. No. 3,324,580 to Baxter and U.S. Pat. No. 4,727,864 to Weisenthal are exemplary of this type of covering.

Designs which avoid the formation of leakage channels at the interface of the user's arm or leg skin and the plastic sleeve involve the use of straps inboard but adjacent to the open end of the sleeve but unfortunately use buckles or buckle loop-Velcro type fastening members which lead to the gathering of excess sleeve material concentrated usually at the buckle or loop area to again provide a water path. Examples of this type of covering are shown in U.S. Pat. Nos. 3,747,125 to Goldman, et al and U.S. Pat. No. 4,254,765 to Brown, et al. Difficulties with still other prior art coverings are discussed in column one of the Brown, et al. patent.

SUMMARY OF THE INVENTION

The present invention is directed to the solution of the type of problems outlined above, but with a less expensive and complicated covering structure which acknowledges the impracticability or impossibility of sealing the end of a plastic sleeve covering directly to the user's skin. The present invention provides a disposable waterproof covering utilizing a flexible sleeve which may or may not be preformed for a particular arm or leg cast or bandage. A snug water-tight contact of the sleeve with the user's arm or leg above the cast or bandage is effected by the use of a stretchable plastic strip capable of considerable stretch before reaching the elastic limit of the plastic. By using a plastic material instead of rubber the spring-back or return rate can be more accurately controlled. The strap has at each of its ends means for permanent attachment to the sleeve such as a pressure sensitive adhesive. With the strap attached at one of its ends to the sleeve adjacent to but below the sleeve opening, the strap is stretched at least 360° around the sleeve before contact with the sleeve to effect permanent attachment. A removable or peelable film covers the pressure sensitive adhesive prior to permanent attachment of the strap to the sleeve in use. In one embodiment, the strap is preattached permanently to the sleeve at one of its ends and the adhesive at the other end of the strap is pressed against a protective film which is attached to the sleeve. The strap end is peeled away from the film when the user is ready to complete the seal. In a preferred embodiment, the strap is of a polyurethane material.

BRIEF DESCRIPTION OF THE DRAWING

The preferred embodiments of the invention are illustrated in the drawing in which.

DESCRIPTION OF THE PREFERRED EMBODIMENTS

Figure 1:
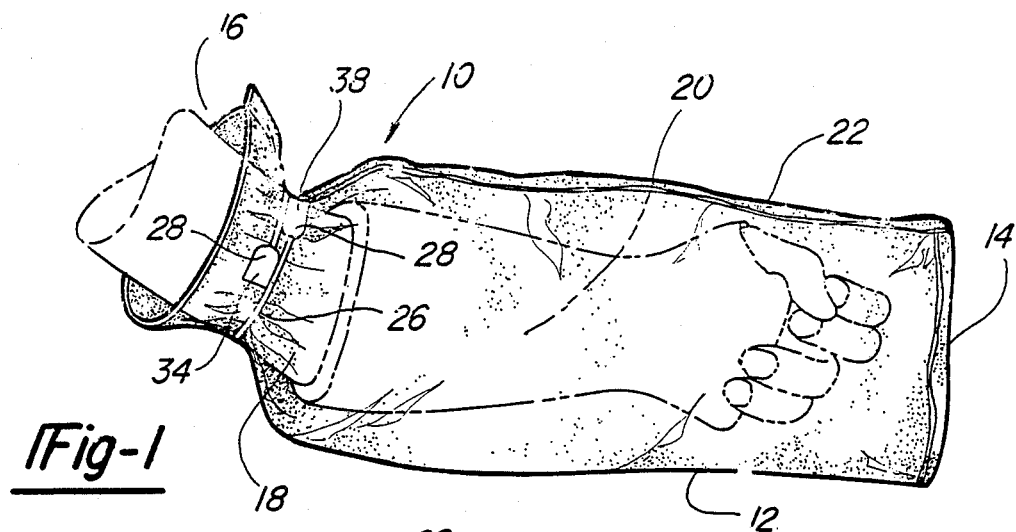
FIG. 1 is an elevational view of the disposable limb covering of this invention as it has been applied over an arm cast of the user showing the stretchable plastic strap as it has seated the waterproof flexible sleeve into sealing relationship with the user's arm.

FIG. 1 shows a disposable limb covering 10 of this invention utilizing a transparent waterproof plastic sleeve 12 which has been heat sealed along seam 14 at its terminal end and has it other end 16 open to receive the limb 18 of the user to completely cover the arm cast 20. The sleeve 12 is made of a soft heat sealble polyethylene or other suitable material which can be transparent, translucent or opaque. In most instances, we prefer to have the sleeve 12 be a seamless tube or to be formed from a folded over sheet with a single longitudinal seem 22 so that an inexpensive single size will fit any limb diameter and length. Normally the covering will be used for only a very short interval of time permitting the user to bathe or shower. The sometimes excessive diameter or length needed to assure coverage in all applications should not be objectionable since the sleeve can be pushed up to bottom the limb at the closed terminal end of the sleeve so that no safety hazard exists.

Figure 3:
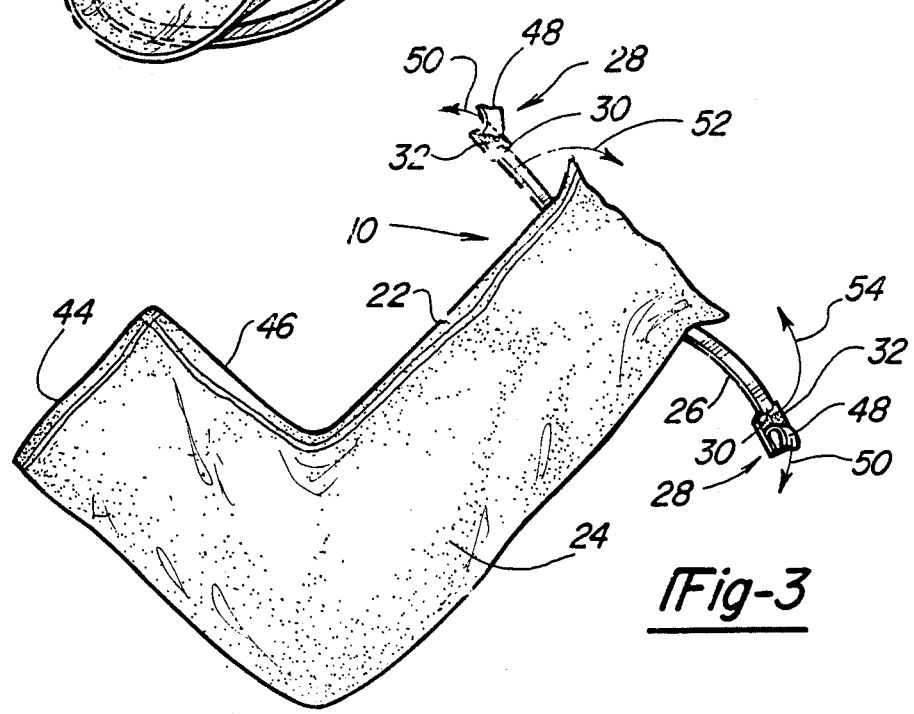
FIG. 3 is plan view showing an embodiment of this invention in which the sleeve has been preshaped to fit a particular cast configuration and the strap in a position with both ends free showing the pressure sensitive adhesive and protective films as they will be removed to permanently affix them to the sleeve and further showing the relationship of the strap to the open end of the sleeve and the direction in which the strap ends will be moved to affix them in an overlapping or at lest 360° wrap around the sleeve to seal it to the limb of a user.

In other instances, particularly where the limb covering may be used for extended periods of time, such as inclement weather use or while engaging in a sport activity, the sleeve may be preformed as shown by sleeve 24 in FIG. 3 to more fully conform to a particular arm or a leg cast or dressing.

Figure 2:
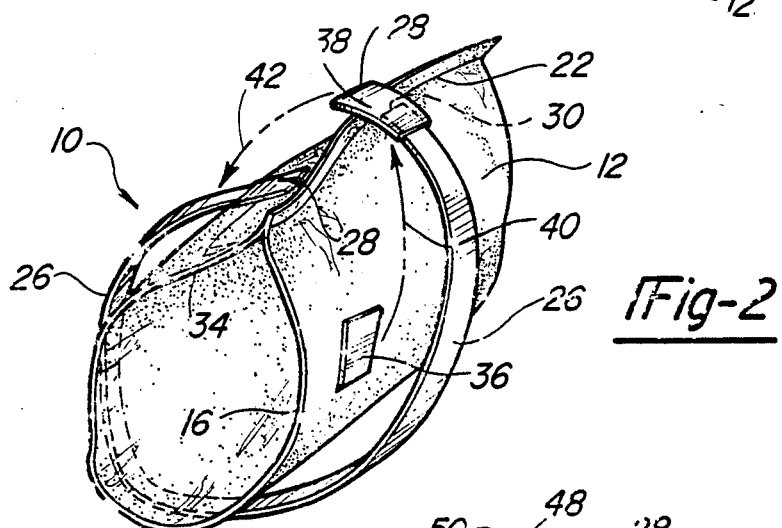
FIG. 2 is a perspective view of the covering of this invention looking into the open end of the waterproof flexible sleeve with one end of the stretchable plastic strap affixed to the sleeve adjacent the open end of the sleeve and the other end of the strap with its pressure sensitive adhesive as it has been released from a protective film on the sleeve and further showing how the strap will be moved to stretch the strap to affix the sleeve in sealing relationship to the user's limb.

Closure strap 26 is made with a highly stretchable, good memory plastic. In the preferred form, this strap would be made of polyurethane in a thickness between 0.002" and 010, preferably 0.002–004". The strap preferably has a width of ½ to ¾ of an inch. Means for attaching the strap to the sleeve are located at both ends of the strap, and this preferably is in the form of a pressure sensitive adhesive. As shown in FIGS. 2 and 3, this is most easily supplied by a separate piece of tape having a pressure sensitive adhesive on one side so as to form a slightly wider than the tape tab 28 which overlies the end 30 of the tape firmly attaching the end to the tab by the pressure sensitive adhesive 32 itself.

As shown in FIG. 2, one of the tabs 34 is permanently attached to sleeve 12 adjacent to the open end 16 of the sleeve. Tab 38 at the other end of strap 26 would be packaged for use by being pressed against a protective film patch 36 from which it can be easily peeled away to be wound around and permanently attached to the sleeve 12.

In use, a cast or bandaged member is inserted into open end 16 of the sleeve 12, and the sleeve is positioned with the strap 26 closely adjacent to the end of the dressing or cast 20 but overlying the patient's arm or leg as shown in FIG. 1. Tab 38 would then be removed from protective film patch 36 as shown by arrow 40 and wound around the sleeve 12 in the direction of arrow 42 to draw the sleeve into a snug contact with the user's arm or leg. The seal is then completed by contacting of the tab 38 to the sleeve as shown in FIG. 1. The tape 26 is continuously stretched as it is being wrapped around the sleeve to assure the intimate contact of the strap with the sleeve and the sleeve with the user's arm or leg.

In the embodiment shown in FIG. 3, the shaped sleeve 24 has been formed by folding over a sheet of sleeve material and heat sealing it along longitudinal seams 22 and 44 and transverse seam 46. In this embodiment, the strap 26 has not been attached at either end of the sleeve 24 prior to use. When the patient has positioned his limb in the sleeve 24, the protective film 48 is removed from one of the tabs 28 by peeling in the direction of the arrow 50 and the tab can be moved in the direction of arrow 52 to be attached to the sleeve as shown by tab 34 in FIGS. 1 and 2. The protective film 48 can then be removed from the other tab 28 and the tab moved in the direction of arrow 54 in FIG. 2 to wind it around the sleeve to be attached to the sleeve as shown by 38 in FIG. 1.

It will be apparent that other variations are possible all within the invention as claimed. For example, in the FIG. 3 embodiment both of the protective films 48 can be attached to the sleeve 12 in the manner of film patch 36 in FIG. 2 so that the strap is positioned at its point of use adjacent open end 16.

The objects of the invention in which an exclusive property or privilege is claimed are defined as follows:

1. A disposable limb covering for temporarily covering and sealing a cast or bandage over an injured limb comprising:

a waterproof, flexible sleeve having a closed terminal end and an open end for receiving said limb;

a strap of plastic material capable of considerable stretch before taking a permanent set by stretching beyond the elastic limit of said material having one end permanently attached to said sleeve adjacent said open end and the other end of said strap having a pressure sensitive adhesive pressed into contract with a protective film be film heavy permanently attached to said sleeve, said strap being of such a length allowing the strap to be stretched around the sleeve at least 360° above the cast or bandage on said limb to effect a snug watertight contact of the sleeve with said limb and allowing the securing of the other end of said strap to said sleeve by peeling away the other end of said strap from said protective film and contact of said pressure sensitive adhesive at said other end to said sleeve.

2. The disposable covering according to claim 1 wherein said strap is a polyurethane.

3. The disposable covering according to claim 1 wherein said sleeve is shaped to selectively receive one of an arm or a leg cast.

* * * * *